United States Patent
Burgess

(10) Patent No.: US 9,827,265 B1
(45) Date of Patent: *Nov. 28, 2017

(54) METHOD FOR ATTENUATING FREE RADICAL FORMATION RESULTING FROM A BODILY INSULT

(71) Applicant: MD Scientific, LLC, Charlotte, NC (US)

(72) Inventor: W. Patrick Burgess, Charlotte, NC (US)

(73) Assignee: MD Scientific, LLC, Charlotte, NC (US)

( * ) Notice: Subject to any disclaimer, the term of this patent is extended or adjusted under 35 U.S.C. 154(b) by 749 days.

This patent is subject to a terminal disclaimer.

(21) Appl. No.: 14/212,588

(22) Filed: Mar. 14, 2014

Related U.S. Application Data

(63) Continuation-in-part of application No. 13/441,323, filed on Apr. 6, 2012, now Pat. No. 9,161,949.

(60) Provisional application No. 61/792,598, filed on Mar. 15, 2013.

(51) Int. Cl.
| | |
|---|---|
| *A61K 33/42* | (2006.01) |
| *A61K 33/10* | (2006.01) |
| *A61K 33/00* | (2006.01) |
| *A61K 9/20* | (2006.01) |
| *A61K 9/14* | (2006.01) |
| *A61K 9/48* | (2006.01) |
| *A61K 9/00* | (2006.01) |

(52) U.S. Cl.
CPC ............ *A61K 33/00* (2013.01); *A61K 9/0095* (2013.01); *A61K 9/14* (2013.01); *A61K 9/20* (2013.01); *A61K 9/48* (2013.01)

(58) Field of Classification Search
CPC ............................... A61K 33/10; A61K 33/00
USPC ...................................................... 424/717
See application file for complete search history.

(56) References Cited

U.S. PATENT DOCUMENTS

| | | | |
|---|---|---|---|
| 3,993,750 A | 11/1976 | Fox, Jr. | |
| 4,101,647 A | 7/1978 | Clauss et al. | |
| 4,289,750 A | 9/1981 | Kopp et al. | |
| 4,308,255 A | 12/1981 | Raj et al. | |
| 4,405,596 A * | 9/1983 | Helbig | A61K 33/14 424/478 |
| 4,451,454 A | 5/1984 | Wong | |
| 4,663,166 A | 5/1987 | Veech | |
| 4,900,540 A | 2/1990 | Ryan et al. | |
| 5,112,622 A | 5/1992 | Kopp | |
| 5,141,739 A | 8/1992 | Jung et al. | |
| 5,147,631 A | 9/1992 | Glajch et al. | |
| 5,154,914 A | 10/1992 | Elgavish et al. | |
| 5,171,563 A | 12/1992 | Abrams et al. | |
| 5,174,987 A | 12/1992 | Takaichl et al. | |
| 5,210,098 A | 5/1993 | Nath | |
| 5,232,685 A | 8/1993 | Speck et al. | |
| 5,352,435 A | 10/1994 | Unger | |
| 5,368,840 A | 11/1994 | Unger | |
| 5,772,984 A | 6/1998 | Berg et al. | |
| 5,891,466 A | 4/1999 | Yesair | |
| 6,420,436 B1 | 7/2002 | Kirkland | |
| 6,475,529 B2 | 11/2002 | Duponchelle et al. | |
| 6,537,272 B2 | 2/2003 | Christopherson et al. | |
| 6,627,393 B2 | 9/2003 | Segall et al. | |
| 7,019,035 B2 * | 3/2006 | Burgess | A61K 33/10 514/686 |
| 7,625,586 B2 * | 12/2009 | Burgess | A61K 33/00 424/686 |
| 8,153,164 B2 * | 4/2012 | Burgess | A61K 33/00 424/686 |
| 9,161,949 B2 * | 10/2015 | Burgess | A61K 33/00 |
| 2002/0077579 A1 | 6/2002 | Tobe | |
| 2002/0137803 A1 | 9/2002 | Kirkland | |
| 2003/0053953 A1 | 3/2003 | Unger | |
| 2003/0118547 A1 | 6/2003 | Vandenberg | |
| 2003/0180390 A1 | 9/2003 | Keum et al. | |
| 2003/0216722 A1 | 11/2003 | Swanson | |

OTHER PUBLICATIONS

Merten et al. (JAMA, 2004: 291(19), 2328-2334 published on May 19, 2004).*
U.S. Appl. No. 13/441,323, filed Apr. 6, 2012.
Rodrigues et al; Amelioration of renal Ischemic Injury by phosphocreatine; Sch. Med., Yale University, New Haven CT, Journal of Surgical Research (1991) Document No. 115:27032.
Winaver et al; Impaired renal acidification following acute renal ischemia in the dog; Fac. Med. Rambam Hospital, Haifa IL (1968), Journal; Document No. 106:82598.
Critical Care Medicine, vol. 32, No. 3, p. 858, "Surviving Sepsis Campaign guidelines for management of severe sepsis and septic shock", 2004.
Nephrol Dial Transplant, vol. 9, Suppl. 4, p. 179, "Risk factors influencing survival in ICU acute renal failure", 1994.
Journal of the American Society of Nephrology, vol. 15, No. 6, p. 1597, Minimal Changes of Serum Creatinine Predict Prognosis in Patients after Cardiothoracic Surgery: A . . . .
Journal of the American Society of Nephrology, vol. 9, No. 4, p. 710, "Hospital-Acquired Acute Renal Failure", 1998.
Critical Care Medicine, vol. 19, No. 11, p. 1352 Effects of Bicarbonate therapy on hemodynamics and tissue oxygenation in patients with lactic acidosis: A prospective . . . .
Annals of Internal Medicine, vol. 112, p. 492, "Bicarbonate Does Not Improve Hemodynamics in Critically Ill Patients Who Have Lactic Acidosis", 1990.
"Acidosis and Sodium Bicarbonate Therapy", Dr. James Cooper, www.nda.ox.ac.uk/wfsa/d1/html/papers/pap008.htm, Published prior to Apr. 2004.

(Continued)

*Primary Examiner* — Mina Haghighatian
*Assistant Examiner* — Helen Chui
(74) *Attorney, Agent, or Firm* — Schwartz Law Firm, P.C.

(57) ABSTRACT

A method is provided for attenuating free radical formation resulting from a bodily insult. The method includes administering bicarbonate to the body of a subject at a dosage ranging from 1.5 mEq/kg of body weight to 5.0 mEq/kg of body weight within a 24-hour period.

16 Claims, No Drawings

(56) References Cited

OTHER PUBLICATIONS

Winaver et al.; Impaired renal acidification following acute renal ischemia in the dog, Kidney International, vol. 30, 1986, pp. 906-913.
Bradley et al., Hypoventilation improves oxygenation after bidirectional superior cavopulmonary connection, The J. of Thoracic and Cardiovascular Surgery, vol. 126, p. 1033-39.
Hagberg et al., Etiology and Incidence of Endotracheal Intubation Following Spinal Anesthesia for Cesarean Section, IMAJ, vol. 3, Sep. 2001, pp. 653-656.
Bams et al, Reliable gastic tonometry after coronoary artery surgery: need for acid secretion suppression despite . . . , Intensive Care Med, 1998, vol. 24, pp. 1139-1143.
Horiguchi et al, A case of traumatic shock complicated by methamphetamine intoxication, Intensive Care Med, 1999, vol. 25, pp. 758-760.
Mark et al., Safety of low-dose itraoperative bicarbonate therapy: A prospective, double blind, randomized study, Critical Care Med, 1993, vol. 21, No. 5, pp. 659-665.
Persson, Acute Arterial Occulsions, Comprehensive therapy, 1976, vol. 2. No. 12, pp. 41-44.
Merten et al. (JAMA, 2004: 291(19), 2328-2334, Prevention of Contrast-Induced Nephropathy With Sodium Bicarbonate—A Ramdomized Controlled Trial; published on May 19, 2014.

\* cited by examiner

METHOD FOR ATTENUATING FREE RADICAL FORMATION RESULTING FROM A BODILY INSULT

TECHNICAL FIELD AND BACKGROUND OF THE INVENTION

This invention relates generally to a method for attenuating free radical formation resulting from a bodily insult, and more specifically, to a method for protecting solid organs against injury caused by disruption of a chemical environment in the solid organ and to a method for protecting tissue from injury related to an exposure of a injurious agent to that solid organ tissue. The method protects the solid organ and tissues within that solid organ by administering a prophylactic solution into the body to alter the acid-base balance. In one particular application, the invention is a method applied when administering a radiographic contrast medium in a manner which reduces the incidence of contrast-induced nephropathy (CIN). In another particular application, the invention is a method applied when administering a radiographic contrast medium in a manner which reduces the cardiac injury (resulting in death) associated with the contrast media injection in cardiac arteries.

The kidneys' main function is to eliminate excess fluid and waste material from the blood. When the kidneys lose this filtering ability, dangerous levels of fluid and waste accumulate in the body causing kidney (renal) failure. Acute kidney failure is most likely to happen after complicated surgery or severe injuries, or when blood vessels leading to the kidneys become blocked or experience low blood pressure, or when the kidneys are exposed to chemical compounds that are potentially toxic. Conversely, chronic kidney failure usually develops slowly with few symptoms in the early stages. Many people with chronic kidney failure have no symptoms until their kidney function has decreased to less than 25 percent of normal. High blood pressure and diabetes are the most common causes of chronic kidney failure.

One adult kidney contains roughly a million nephrons, each consisting of a tuft of capillary blood vessels (glomerulus) and tubules that lead to the collecting system and, eventually, to the bladder. Each tuft of capillaries filters fluid from the bloodstream, and passes the filtrate to a tubule. The filtrate contains both waste products and substances vital for health. From the tubules, waste byproducts such as urea, uric acid and creatinine are excreted in urine while substances the body needs such as glucose, proteins, amino acids, calcium and salts are absorbed by the tubules back into the bloodstream. While this unique filtration system is generally able to clear all the waste products produced by the body, problems can occur if the fragile tubules or glomeruli are damaged or diseased.

Many conditions and circumstances can damage kidneys, including intrinsic kidney disease or injury, high blood pressure, diabetes mellitus, exposure to toxins and certain medications, kidney stones, tumors and even infections in other parts of your body. Many conditions and circumstances can damage tissue, including exposure to toxins and certain medications that can stimulate free radical formation, often accentuated in the ischemic tissue and in tissue where the acid-base balance is in favor of the acid. Many of these conditions for the kidney or the other tissue areas may show no signs or symptoms until irreparable damage has occurred.

The mechanism of the vast majority of acute kidney damage and tissue injury is often modulated by the formation of free radicals known to be increased in an acid environmental (pH that is low compared to normal body pH). One of the functions of the kidney is to regulate acid-base metabolism by actively absorbing the filtered bicarbonate and generating bicarbonate, while excreting the typical acid load of subjects. This process of eliminating the "acid load" causes the generation of renal tubular fluid which is relatively acidic compared to normal tissue. This acid environment could accelerate the formation of free radicals under certain conditions. Other potentially injured tissue may have reduced blood delivery or high concentrations of toxic chemicals or drug and thus potentially have inadequate base to buffer the free radicals formed by toxic condition or toxic chemical or drug. Existing medical references support the attenuation of free radical formation by inducing a more normal pH environment in the kidney and in tissue that has overwhelming exposure to toxic conditions or toxic chemicals or drugs.

The use of iodinated, radiographic contrast (RC) media has long been recognized as a contributing factor in acute kidney dysfunction. Examples of imaging and medical procedures requiring the use of RC include Computerized Tomographic ("CT") scan enhancement, arteriograms, cardiac catherization, vascular studies, stents, lumbar myelography, thoraco-cervical myelography, cerebral angiography, peripheral arteriography, venography, angiocardiography, left ventriculography, selective visceral arteriography, digital subtraction abgiography, urography, arthrography, and computer tomography angiography ("CTA"). The degree of acute kidney dysfunction—labeled "contrast induced nephropathy" (CIN)—ranges from a short-term slight increase in serum creatinine levels to overt kidney failure requiring temporary or permanent dialysis, and in some cases resulting in death. CIN is broadly defined as a rise in serum creatinine levels in relation to the administration of contrast media. CIN has been reported to be the third most common cause of kidney insufficiency occurring in hospitalized patients, and it might be a factor in up to 10 percent of all cases of acute kidney failure.

Iodinated contrast in high concentration will have a similar effect on other solid organ tissues, thus the formation of free radicals can further the injury the tissue of these solid organs, in particular the heart when the iodinated contrast is injected directly in the cardiac vessels. The heart tissue behind heart artery obstruction(s) or heart tissue with inadequate blood flow from any cause is likely to become "ischemic" when the work of the heart is increased or when contrast medium is injected into these areas. An abnormal or low blood flow may alter the acid-balance in this "ischemic" tissue thus leading to an increase in free radical formation leading to further tissue damage. This condition is mediated by the method described in this patent. Increased bicarbonate can alter the acid-balance in these "ischemic" areas to reduce or eliminate the free radical formation and subsequent damage.

Prior art efforts to treat kidney dysfunction recognize the use of a sodium bicarbonate infusion. These existing methods, however, are fraught with complications, drawbacks, and inconclusive test results.

Complications of Bicarbonate Infusions

Hypertonic solutions of sodium bicarbonate (8.4% or 1 Molar) are supplied in most hospitals in 50 mL ampules to be administered slowly, or added to other intravenous solutions. Rapid infusions or excessive volumes of this hypertonic solution are known to cause serious injury. This injury can occur in the form of a rapid depression of serum potassium and subsequent cardiac rhythm disturbances (even fatal disturbances), depression of serum ionized calcium with an associated drop in blood pressure, hemolysis or breakdown of red cells as a result of the high osmolar solution, and severe pain and tissue necrosis at the site of an intravenous extravagation.

If sodium bicarbonate is prepared in a solution with a concentration of 25 to 50 mEq/L, as directed in prior U.S. Pat. No. 5,112,622, then the volume required to reach a target level of 2 mEq/kg (of subject weight) in a 70 kg subject would be 5.6 liters to 2.8 liters. This volume is large and a challenge for normal subjects to tolerate in an eight hour period, and entirely unacceptable and dangerous as an administered dose of fluids to "sick" or elderly subjects undergoing a substantial medical procedure, such as cardiac catheterization or cardiac surgery. The critical care literature is full of references to the danger of sodium bicarbonate infusions in critically ill subjects.

The bicarbonate pretreatment of the present invention has been shown to nearly eliminate acute kidney failure associated with contrast exposure. Similar evidence shows that similar doses can reduce cardiac associated death with exposure to iodinated contrast. The choice of bicarbonate concentration in the 100 to 300 mEq/L range allows an effective dose of solution to be administered in a volume of fluid that is well tolerated by "sick" subjects undergoing the diagnostic or therapeutic procedure.

Since many other causes of kidney dysfunction (other than CIN and ischemia from low blood pressure) are induced by the free radical formation process, the present method can also be expected to respond favorably against these disruptions by similar administration of bicarbonate, provided excessive volume and excessive concentration can be avoided. Suggested prior art treatments using sodium bicarbonate, such as described in the '622 Patent, would require a volume of fluid in excess of what even a normal subject could be expected to tolerate without death or serious complications. The present invention may identify an effective and tolerable dose of the bicarbonate anion, concentration of the anion, and timely administration necessary for a successful prophylaxis.

The terms "organ" and "organ tissue" are broadly defined herein to mean the solid human organ that is distal to and perfused by the artery which receives the administration (e.g., injection) of contrast media. The "organ tissue" is that human tissue distal to the site of arterial injection of the iodinated contrast agent, and refers specifically to the tissue perfused beyond the injection site which could represent a portion of a human solid organ (heart or brain) or one leg or a portion of one leg, depending on the injection site of the contrast media.

SUMMARY OF INVENTION

Therefore, it is an object of the invention to provide a method for protecting kidney tissue against injury caused by disruption of the chemical environment in the kidneys.

It is another object of the invention to provide a method for protecting tissue (cardiac, cerebral, or other solid organ tissue) from further injury that may occur associated with injury caused by disruption of the chemical environment in that tissue.

It is another object of the invention to provide a method for protecting nephrons against injury caused by administration of iodinated, radiographic contrast (RC) media.

It is another object of the invention to provide a method for protecting solid organ tissue (like, heart and brain) against injury caused by administration of iodinated, radiographic contrast (RC) media.

It is another object of the invention to alter the kidney tubular acid-base balance in favor of a more normal pH prior to a bodily insult or chemicals in order to attenuate kidney injury and kidney tissue damage.

It is another object of the invention to alter the body acid-base balance in favor of a higher base (bicarbonate) concentration prior to a bodily insult or chemicals in order to attenuate solid organ damage and solid organ tissue damage.

It is another object of the invention to provide a method for administering a contrast medium which substantially eliminates the incidence of contrast-induced nephropathy (CIN) and reduces further injury to solid organ tissue.

It is another object of the invention to provide a method for administering a contrast medium which reduces the subject's time in the hospital by 12 hours or more, as compared to other treatments which infuse saline solution for 12 hours before and 12 hours after the contrast exposure.

It is another object of the invention to provide a method for administering a contrast medium which utilizes a protective bicarbonate received intravenously or orally.

It is another object of the invention to provide a method for administering a contrast medium which is especially applicable to chronically ill subjects who currently may not receive a contrast medium for fear of inducing CIN.

It is another object of the invention to provide a method for administering a contrast medium in a manner which may improve a healthcare institution's rating for insurance and referral purposes.

It is another object of the invention to provide a method for administering a contrast medium in a manner which may reduce the physician's exposure to legal liability.

It is another object of the invention to provide a method for administering a contrast medium in a manner which may reduce overall healthcare costs.

It is another object of the invention to provide a method for administering a contrast medium in a manner which may reduce death from cardiac injury or failure in the six months following the contrast exposure.

It is another object of the invention to provide a method for administering a contrast medium in a manner which may not damage or impair healthy kidneys.

It is another object of the invention to provide a method for administering a contrast medium in a manner which is easily administered by the hospital staff.

It is another object of the invention to provide a method for administering a contrast medium which is applicable to both ionic and non-ionic contrast media.

It is another object of the invention to provide a method for attenuating free radical formation in the body of a subject.

It is another object of the invention to provide a method which reduces the anion gap in the arterial blood.

These and other objects of the present invention are achieved in the preferred embodiments disclosed below by providing a method for protecting nephrons against injury caused by disruption of a chemical environment in the kidney. The method includes the step of administering a prophylactic alkaline solution into the body of a subject. The solution has a concentration of bicarbonate greater than 70 mEq/L.

Preferably, the prophylactic solution has a bicarbonate concentration within a range of 100 mEq/L and 300 mEq/L. The bicarbonate is administered into the body at a dose of between 0.8 and 5 mEq of bicarbonate per kg of subject weight, and more preferably, between 1.5 and 3 mEq of bicarbonate per kg of subject weight.

According to another preferred embodiment of the invention, the prophylactic solution contains sodium.

According to another preferred embodiment of the invention, the prophylactic solution contains potassium.

Preferably, the prophylactic solution contains between 75%-100% sodium and between 25%-0% potassium.

According to another preferred embodiment of the invention, the total volume of prophylactic solution administered into the body ranges from 4 to 30 ml/kg (of subject weight).

According to another preferred embodiment of the invention, the prophylactic solution is administered into the body at a rate of between 0.5 and 5 ml/kg (of subject weight)/hr.

In another embodiment, the invention is a method for reducing contrast-induced nephropathy resulting from administration of a contrast medium into the body of a subject. The method includes the steps of, prior to receiving the contrast medium, administering an initial dose of prophylactic alkaline solution into the body. The solution has a concentration of bicarbonate greater than 70 mEq/L. After receiving the contrast medium, a maintenance dose of the prophylactic solution is administered into the body.

According to another preferred embodiment of the invention, the maintenance dose is administered into the body at a rate lower than that of the initial dose.

According to another preferred embodiment of the invention, the initial dose of prophylactic solution is administered into the body at a time beginning no later than 6 hours and no less than 15 minutes prior to receiving the potential bodily insult.

According to another preferred embodiment of the invention, the maintenance dose is administered into the body for a period of between 5 and 12 hours after receiving the potential bodily insult.

In yet another embodiment, the invention is a method used when administering a contrast medium into the body of a subject. The method includes the steps of, prior to receiving the contrast medium, administering an initial dose of prophylactic alkaline solution into the body. The solution has a concentration of bicarbonate greater than 70 mEq/L. The contrast medium is then administered into the body. After receiving the contrast medium, a maintenance dose of the prophylactic solution is administered into the body.

In yet another embodiment, the invention is a method for attenuating free radical formation resulting from a bodily insult. The method includes the step of administering an alkaline solution into the body of a subject. The solution has a concentration of bicarbonate greater than 70 mEq (milliequivalents)/L.

According to one embodiment, the bodily insult comprises sepsis or septic shock syndrome.

According to another embodiment, the bodily insult is ischemia—usually this is a state of low blood pressure as a result of one or more of many different medical conditions.

According to another embodiment, the bodily insult is a condition selected from the group consisting of immunosuppression, rhabdomyolysis, heat stroke, acidosis, heart failure, blood clot, pulmonary embolism, pneumonia, shock, trauma, and low blood pressure.

According to another embodiment, the bodily insult is a reaction caused by a drug selected from the group consisting of antibiotics and nonsteroidal anti-inflammatory drugs (NSAIDs).

According to another embodiment, the bodily insult is a reaction resulting from treatment of cancer using chemical agents.

According to another embodiment, the bodily insult is cell lysis.

According to another embodiment, the bodily insult is any surgery.

According to another embodiment, the bodily insult is an organ transplant, or results from reperfusion insult associated with kidney transplantation.

According to another embodiment, the bodily insult is cardiovascular or vascular surgery.

According to another embodiment, the solution is administered into the body during trauma care. The term "trauma care" is broadly defined to mean an initial medical response to an injury, such at that performed at the scene of the accident, in an ambulance, or at the emergency room.

According to another embodiment, the bodily insult is a drug overdose.

According to another embodiment, the bodily insult is radiation exposure resulting from radiation therapy, whether the exposure was the result of medical therapy or exposure at the work place.

In yet another embodiment, the invention is a method for manipulating an acid-base balance in the body. The method includes the step of administering an alkaline solution into the body of a subject. The solution has a concentration of bicarbonate greater than 70 mEq/L.

In yet another preferred embodiment, the invention includes the step of administering bicarbonate to the body of a subject at a dosage of at least 1.5 mEq/kg of body weight within a 24-hour period.

According to another preferred embodiment of the invention, between 75% to 100% of the bicarbonate dosage is administered within a 12-hour period.

According to another preferred embodiment of the invention, between 75% to 100% of the bicarbonate dosage is administered within a 6-hour period.

According to another preferred embodiment of the invention, between 25% to 60% of the bicarbonate dosage is administered prior to the bodily insult. A remaining 40% to 75% of the bicarbonate dosage is administered at hourly intervals after the bodily insult.

According to another preferred embodiment of the invention, the dosage of bicarbonate is at least 3 mEq/kg of body weight.

According to another preferred embodiment of the invention, the bicarbonate is administered can be administered in part or full dose in a form selected from a group consisting of tablet, powder, capsule, and oral solution.

DESCRIPTION OF THE PREFERRED EMBODIMENT AND BEST MODE

In one exemplary embodiment, the invention is a method for protecting nephrons against injury caused by a disruption of a chemical environment in the kidney. Such disruptions commonly result from exposure to iodinated radiographic contrast media (administered prior to CT scans); emergency exploratory surgeries; shock; trauma; certain transplant immunosuppression regimens (e.g., cyclosporine and Prograf®); organ transplant; cardiovascular surgery; certain antibiotic therapy (gentamicin, tobramicin, amikacin, vancomycin); and NSAID's (Motrin®, Indocin®, tordol, Advil®, naprasyn). In its broadest application, the concept of the present method is applicable for protecting any organ by manipulating the body's acid-base balance through infusion of a prophylactic alkaline solution in a prescribed concentration and dosage.

The alkaline solution is contained inside a sterile container and is administered into the body either intravenously or orally. In the example described below, the method is a prophylactic treatment for preventing kidney damage resulting from exposure to contrast media. Examples of such iodinated radiographic contrast media include iopamidol (a tri-iodinated, non-ionic, water-soluble, contrast medium), iomeprol, iohexol, iobitridol, iodixanol, ioversol, ioxaglate, iotrolan, iopromide, iobitridol, and diatrizoate. The treatment conditions the nephrons in the kidney to become more alkaline in order to better tolerate stress caused by the iodinated contrast media. By this method, the goal is to provide between 25% and 60% of the total dose of the prophylactic solution over a time period beginning at least 15 minutes prior to receiving the contrast medium. The remainder of the total dose of the solution is administered during IV infusion of the contrast medium and over a subsequent 5 to 12 hour period. The total dose is preferably between 0.8 and 5 mEq of bicarbonate per kilogram of subject weight, and more preferably, between 1.5 and 3 mEq of bicarbonate per kilogram of subject weight.

According to one embodiment, the solution comprises a bicarbonate anion combined with a sodium and/or potassium cation. The cation is preferably a mixture of sodium (75% to 100%, typically 235 mEq/L) and potassium (25% to 0%, typically 15 mEq/L). The preferred concentration of the bicarbonate anion is greater than 70 mEq/L, and more preferably, between 100 mEq/L and 300 mEq/L. Contrary to the teachings of the prior art, a higher bicarbonate concentration is desirable in order to infuse the necessary chemicals without flooding the body with an excessive volume of fluid. Ideally, the concentration should be around 100 to 300 mEq/L, so that the total volume infused is from 4 to 30 ml/kg (of subject weight). For a goal infusion of 1.8 mEq/kg (of subject weight) using 250 mEq/L solution, the volume infused over a 7 to 8 hour period is 7.2 ml/kg (of subject weight)—or an average of 1 ml/kg (of subject weight)/hour.

EXAMPLE

A prophylactic solution consisting of 5.41 grams of sodium, 0.59 grams of potassium, 15.25 grams of bicarbonate, and approximately 979 grams of water per liter is prepared and administered into the body via an IV infusion. The treatment is provided as follows:

(a) at least one hour prior to (but not more than three hours before) intravenous infusion of the iodinated contrast medium, infuse an initial bolus dose of prophylactic solution at a rate of 2.5 mL per kilogram of subject weight over 30 to 60 minutes;

(b) after the initial bolus infusion, reduce the infusion rate to 0.62 mL per kilogram of subject weight per hour, and continue infusion throughout administration of the contrast medium and for six (6) hours after the contrast administration is completed;

(c) monitor subject during the infusion period for occurrence of adverse symptoms or signs including severe hypertension, pulmonary edema, decompensated heart failure, shortness of breath and wheezing; and (d) upon occurrence of adverse symptoms or signs, reduce the infusion rate to 10 mL per hour and seek medical evaluation for the subject.

The following Table indicates the prescribed subject dosage rate for the initial bolus and maintenance infusion:

| Subject Weight | | Initial Bolus, mL | Maintenance Infusion Rate, |
|---|---|---|---|
| kilograms, kg | pounds, lbs | over 1 hour | mL per hour |
| <32.8 kg | <72.2 lbs | 2.5 X wt(kg) | 0.62 X wt(kg) |
| 32.8 to 40.8 kg | 72.2 to 89.8 lbs | 100 mL | 25 mL/hr |
| 40.8 to 48.8 kg | 89.8 to 107.5 lbs | 122 mL | 30 mL/hr |
| 48.9 to 56.9 kg | 107.6 to 125.2 lbs | 142 mL | 35 mL/hr |
| 57.0 to 64.9 kg | 125.3 to 142.9 lbs | 162 mL | 40 mL/hr |
| 65.0 to 73.0 kg | 143.0 to 160.7 lbs | 182 mL | 45 mL/hr |
| 73.1 to 81.0 kg | 160.8 to 178.4 lbs | 202 mL | 50 mL/hr |
| 81.1 to 89.1 kg | 178.5 to 196.2 lbs | 223 mL | 55 mL/hr |
| 89.2 to 97.2 kg | 196.3 to 213.9 lbs | 243 mL | 60 mL/hr |
| 97.3 to 105.2 kg | 214.0 to 231.6 lbs | 263 mL | 65 mL/hr |
| 105.3 to 113.3 kg | 231.7 to 249.4 lbs | 283 mL | 70 mL/hr |
| 113.4 to 121.4 kg | 249.5 to 267.1 lbs | 303 mL | 75 mL/hr |
| 121.5 to 129.4 kg | 267.2 to 284.9 lbs | 323 mL | 80 mL/hr |
| 129.5 to 137.5 kg | 285.0 to 302.6 lbs | 343 mL | 85 mL/hr |
| 137.6 to 145.6 kg | 302.7 to 320.4 lbs | 363 mL | 90 mL/hr |
| 145.7 to 153.6 kg | 320.5 to 338.1 lbs | 383 mL | 95 mL/hr |
| 153.7 to 161.7 kg | 338.2 to 355.8 lbs | 403 mL | 100 mL/hr |
| >161.7 kg | >355.8 lbs | 2.5 X wt(kg) | 0.62 X wt(kg) |

In addition to the above, the prophylactic solution may include one or a combination of the following additives: calcium-HCO3, magnesium, dextrose (1%-7%), Na or K lactate (1-60 mEq/L), Na or K citrate or acetate (1-60 mEq/L), acetazolamide, and/or other anionic components such as chloride, phosphate, pyruvate, and/or other unnamed organic anions.

In other applications, the present method may be used to attenuate free radical formation in the body resulting from a variety of insults. As indicated above, free radical formation can lead to serious medical disorders and conditions including (but not limited to) acute kidney failure.

In one example, the present bicarbonate solution is administered to certain at-risk hospital patients for sepsis—a severe illness caused by overwhelming infection of the bloodstream by toxin-producing bacteria. Sepsis occurs in 2 of every 100 hospital admissions, and can originate anywhere in the body including the kidneys, liver, gall bladder, bowel, skin, and lungs. The death rate can be as high as 60% for people with underlying medical problems. Preferably, the initial bolus (as indicated in the Table above) is administered prior to the bodily insult (sepsis), or immediately after diagnosis, and followed by the prescribed maintenance infusion for the particular subject until the critical phase of the infection has resolved (this is usually 2 to 4 days but could be shorter or longer).

In another example, the bodily insult may comprise any ischemic condition, such as ischemic cardiomyopathy (heart failure). Other conditions known to cause ischemia include obstruction in the blood system, blood clot, pulmonary embolism, and pneumonia. Again, the initial bolus is preferably administered prior to the bodily insult, or immediately thereafter, followed by the prescribed maintenance infusion for the particular subject until the critical phase of the bodily insult has resolved (this is usually 2 to 4 days but could be shorter or longer).

In yet another example, the bodily insult is an induction of immuno-suppression. Subjects with this disorder have a reduced or absent immune response. Drugs linked to this disorder include cyclosporine-A and tacrolimus, both known to cause free-radical mediated renal failure. To attenuate free radical formation, an initial bolus of the prophylactic bicarbonate solution is administered to the subject prior to receiving the drug, followed by the prescribed maintenance infusion until the critical phase of the induction of immunosuppression is completed (this is usually 2 to 7 days but could be shorter or longer).

Other disorders and conditions, including rhabdomyolysis, acidosis, heat stroke, low blood pressure, heart attack, shock, and trauma promote increased free radical formation in the body. In these cases, free radical formation may be attenuated by administration of an initial bolus of the prophylactic solution prior to the bodily insult followed by the prescribed maintenance infusion. Given the relative difficulty (and in some cases, impossibility) of predicting when such disorders or conditions might occur, the prophylactic solution may be administered shortly after diagnosis with considerable but perhaps lesser effectiveness, and continued until the critical phase of the bodily insult has resolved (this is usually 2 to 4 days but could be shorter or longer).

All surgeries, especially organ transplants, cardiovascular surgery, and trauma surgery, promote free radical formation in the body. In these cases, free radical formation may be attenuated by administration of an initial bolus of the prophylactic bicarbonate solution prior to surgery followed by the prescribed maintenance infusion and continued until the critical phase of the bodily insult has resolved (this is usually 1 to 3 days but could be shorter or longer).

The present method is further applicable as a prophylactic treatment with certain drug therapies including antibiotics and chemotherapy. For example, prior to the anticipated cell lysis from chemotherapy, an initial bolus of bicarbonate solution is administered to the subject followed by the prescribed maintenance infusion. In the case of a drug overdose, early infusion of the bicarbonate solution in the ambulance or emergency room will protect against acute kidney failure, and may save lives.

Oral Administration of Bicarbonate

Effective attenuation of free radical formation resulting from bodily insult may also be achieved through oral administration of a bicarbonate compound in a manner consistent with the present method. Oral administration is especially appropriate for healthier subjects with the capacity to resume normal activity shortly after the insult, while taking the prescribed bicarbonate treatment. For these subjects, treatment can be self-administered outside of the hospital or physician's office, and at a considerably lower cost.

As previously indicated, the total bicarbonate dosage administered to the body is between 0.8 to 5 mEq per kg of subject weight, and more preferably, between 1.5 and 3 mEq per kg of subject weight. The examples below use a dosage of 3 mEq per kg of subject weight. The exact mEq weight of the bicarbonate compound is dependent upon the salt form (cation) used. For example, one (1) mEq of the following salts is equivalent to the indicated weight in grams:

| Salt | Molecular weight | grams = 1 mEq |
|---|---|---|
| Sodium Bicarbonate | 84 | 0.084 |
| Potassium Bicarbonate | 100 | 0.100 |

As indicated above, 75% to 100% of the bicarbonate is in sodium form, and 0% to 15% in potassium form. The anionic component preferably consists of 100% bicarbonate (or bicarbonate equivalent, such as acetate, gluconate, citrate, and lactate). In addition to sodium and potassium, the salt component (or cation) may include a wide variety other suitable elements including magnesium and calcium. The anionic component may also include other potassium additives, such as chloride, phosphate, pyruvate, and/or other unnamed organic anions. Preferably, 25% to 40% of the total bicarbonate dosage is administered to the subject at least 15 minutes before the bodily insult, and for a maintenance period of 5 to 12 hours after the insult.

The following examples demonstrate application of the present method through oral administration of bicarbonate to the body of an 80 kg subject.

Example 1

100% Sodium Bicarbonate: At a dosage of 3 mEq per kg, the subject takes a total of (3×80) 240 mEq of sodium bicarbonate, or (240 mEq×0.084) 20.16 grams. Of this amount, (25%×20.6) 5.15 grams is administered at least 15 minutes before the insult. Over the following 6 hours (maintenance period) after the insult, the remaining 15.45 grams is administered at a dose rate of 2.575 grams per hour (i.e., 20.16 grams over 7 hours).

Example 2

95% Sodium Bicarbonate and 5% Potassium Bicarbonate: Using the same protocol outlined in Example 1 above, the subject takes (95%×3 mEq) 2.85 mEq of sodium bicarbonate and (3-2.85) 0.15 mEq of potassium bicarbonate. This equates to (2.85×80×0.084) 19.152 grams of sodium bicarbonate and (0.15×80×0.100) 1.2 grams of potassium bicarbonate. The resulting total dosage is 20.352 grams. Of this amount, the subject takes (25%×20.352) 5.088 grams at least 15 minutes before the insult, and the remainder (15.264 grams) over the next 6 hours at a dose rate of 2.54 grams per hour.

Form of the Bicarbonate Compound

The bicarbonate compound can be prepared in the following forms:

(a) For 100% Sodium Bicarbonate

Tablet: The tablet can be in any size, and provides a convenient unit for handling. A 1000 mg (or 1.000 gram) tablet of sodium bicarbonate contains (1.000 gram/0.084) 11.9 mEq of sodium bicarbonate. In Example 1, the subject takes a total of (240 mEq/11.9) 20 tablets. Approximately 5 tablets (25% of total dosage) are taken prior to the insult, and 3 tablets per hour for the next 5 hours thereafter. The tablet can be taken directly by mouth or dissolved in a beverage of choice. For enhanced mechanical stability for handling, the tablet may further comprise small amounts of incipient ingredients.

Powder: The powder can be weighed to a precise amount for each subject. In Example 1 above, the subject takes 20.16 grams of the bicarbonate compound-5.15 grams 15 minutes before the insult, and 2.575 grams per hour over the next 6 hours. To facilitate handling and distribution, the powder may be packaged in 2.575-gram packets.

Capsule: The bicarbonate can also be encapsulated in material readily dissolved in the stomach or intestine to facilitate ease of handling.

Beverage: A beverage can be provided with the bicarbonate powder or tablet added and dissolved immediately prior to use by the subject. The bicarbonate may be mixed with water or a flavored drink like a sport drink.

(b) For 95% Sodium Bicarbonate with 5% Potassium Bicarbonate (on a mEq Basis)

Tablet: The tablet can be in any size, and provides a convenient unit for handling. A 1000 mg (or 1.000 gram) tablet of sodium bicarbonate and potassium bicarbonate contains (0.9411 grams of sodium bicarbonate and 0.0589 grams of potassium bicarbonate) 11.79 mEq of bicarbonate salts. In Example 2, the subject takes a total of (240 mEq/11.79) 20 tablets. Approximately 5 tablets (25% of the total dosage) is taken prior to the insult, and 3 tablets per hour for the next 5 hours thereafter.

Powder: The powder can be weighed to a precise amount for each subject. In Example 2, the subject takes 20.352 grams of the bicarbonate compound-5.088 grams 15 minutes before the insult, and 2.54 grams per hour over the next 6 hours.

Capsule: The bicarbonate can be encapsulated in material readily dissolved in the stomach or intestine to facilitate ease of handling.

Beverage: A beverage can be provided with the powder or tablet added and dissolved immediately prior to use by the subject, as previously described.

Example 3

In a further example, a total of 1.96 mEq/kg of sodium bicarbonate is administered: 40% prior to the contrast and 60% during and after the contrast. In a study of high risk subjects, randomized to standard of care using the same dose of normal saline compared to a sodium bicarbonate solution (both with a sodium concentration of 154 mEq/L). In that study the incidence of death in the subjects that had received an injection of iodinated contrast in the cardiac arteries was reduced from 10.1% for those treated with sodium chloride (saline) to 3.2% in those treated with the sodium bicarbonate solution. Death was primarily from cardiac failure. The incidence of death in the subjects that had other types of iodinated contrast injection (other non-cardiac arteries) had the same incidence of death in both study cohorts.

Various exemplary embodiments of the present invention are described above. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

For purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function or effect of the subject matter at issue. It is also noted that terms like "preferably", "commonly", and "typically" are not utilized herein to limit the scope of the claimed invention or to imply that certain features are critical, essential, or even important to the function or effect of the claimed invention. Rather, these terms are merely intended to highlight alternative or additional features that may or may not be utilized in a particular embodiment of the present invention.

For the exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

In the exemplary embodiments of the present invention described above, no element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

A method for protecting nephrons against injury caused by a disruption of the chemical environment in the kidney; a method for reducing contrast-induced nephropathy; a safe method for administering a contrast medium into the body of a subject; and a method for attenuating free radical formation resulting from a bodily insult are described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. A method for attenuating free radical formation caused by an iodinated contrast agent and resulting in cardiac injury, said method comprising administering bicarbonate into the body of a subject in need thereof at a dosage ranging from 1.5 mEq/kg of body weight to 5.0 mEq/kg of body weight within a 24-hour period, and wherein a pre-insult dosage of 25%-60% of the bicarbonate is administered prior to the bodily insult, and a remaining 40%-75% of the bicarbonate is administered after the pre-insult dosage within the 24-hour period.

2. The method according to claim 1, wherein the pre-insult dosage and remaining bicarbonate is administered in a solution comprising a bicarbonate concentration within a range of 100 mEq/L and 300 mEq/L.

3. The method according to claim 1, wherein the bicarbonate is administered in a solution comprising potassium.

4. The method according to claim 3, wherein the solution comprises less than 25% potassium.

5. The method according to claim 1, wherein the bicarbonate is administered in a solution at a volume ranging from 4.0 to 30.0 ml/kg of subject weight.

6. The method according to claim 5, wherein the solution is administered into the body at a rate of between 0.5 and 5 ml/kg of subject weight/hr.

7. The method according to claim 1, and comprising continuing the administration of bicarbonate to the subject after expiration of the 24-hour period.

8. The method according to claim 1, wherein 75% to 100% of the bicarbonate dosage is administered within a 12-hour period.

9. The method according to claim 1, wherein 75% to 100% of the bicarbonate dosage is administered within a 6-hour period.

10. The method according to claim 1, wherein the pre-insult dosage and remaining dosage of bicarbonate ranges from 2.0 mEq/kg of body weight to 4.0 mEq/kg of body weight.

11. The method according to claim 1, wherein the bicarbonate is administered to the subject via an intravenous line.

12. The method according to claim 1, wherein the bicarbonate is administered to the subject via a solution comprising additives selected from a group consisting of calcium bicarbonate, magnesium salt, dextrose, sodium lactate, potassium lactate, sodium citrate, potassium citrate, and sodium acetate.

13. The method according to claim 1, wherein the bicarbonate is administered to the subject via a solution comprising additives selected from a group consisting of chloride, phosphate, and pyruvate.

14. A method for attenuating free radical formation caused by an iodinated contrast agent and resulting in cardiac injury, said method comprising administering bicarbonate to the body of a subject in need thereof at a dosage ranging from 2.0 mEq/kg of body weight to 4.0 mEq/kg of body weight within a 12-hour period, and wherein a pre-insult dosage comprising between 25%-40% of the bicarbonate is administered prior to the bodily insult and a remaining 60%-75% of the bicarbonate is administered after the pre-insult dosage within the 12-hour period.

15. The method according to claim 14, and comprising continuing the administration of bicarbonate to the subject after expiration of the 12-hour period.

16. The method according to claim 14, wherein the pre-insult dosage and remaining bicarbonate is administered to the subject via an intravenous line.

* * * * *